United States Patent [19]
Kobylinski et al.

[11] Patent Number: 4,605,679
[45] Date of Patent: * Aug. 12, 1986

[54] ACTIVATED COBALT CATALYST AND SYNTHESIS GAS CONVERSION USING SAME

[75] Inventors: Thaddeus P. Kobylinski, Prospect; Charles L. Kibby, Gibsonia; Richard B. Pannell, Allison Park; Elizabeth L. Eddy, Gibsonia, all of Pa.

[73] Assignee: Chevron Research Company, San Francisco, Calif.

[*] Notice: The portion of the term of this patent subsequent to Aug. 12, 2003 has been disclaimed.

[21] Appl. No.: 734,188

[22] Filed: May 15, 1985

Related U.S. Application Data

[60] Continuation-in-part of Ser. No. 635,911, Jul. 30, 1984, which is a continuation-in-part of Ser. No. 310,969, Oct. 13, 1981, abandoned, and Ser. No. 540,662, Oct. 11, 1983, Pat. No. 4,493,905, which is a division of Ser. No. 310,977, Oct. 13, 1981, Pat. No. 4,413,064.

[51] Int. Cl.$^4$ .............................................. C07C 1/04
[52] U.S. Cl. .................................. 518/700; 518/715; 502/332
[58] Field of Search ............... 518/700, 715, 716, 709, 518/720

[56] References Cited

U.S. PATENT DOCUMENTS

| | | | |
|---|---|---|---|
| 2,273,864 | 2/1942 | Houdry | 518/709 |
| 2,289,731 | 7/1942 | Roelen et al. | 518/709 |
| 4,088,671 | 5/1978 | Kobylinski . | |
| 4,142,962 | 3/1979 | Yates et al. . | |
| 4,207,208 | 6/1980 | Lucki et al. | 518/720 |
| 4,460,710 | 7/1984 | Sapienza et al. . | |
| 4,492,774 | 1/1985 | Kibby et al. | 518/715 |

FOREIGN PATENT DOCUMENTS

1548468 7/1979 United Kingdom .

OTHER PUBLICATIONS

Anderson, J. R. Elmes, P. S. Howe, R. F., and Mainwaring, D. E., Journal of Catalysis, 50, pp. 508–518, 1977.
Hucul, D. A. and Brenner, A., Journal of Physical Chemistry, 85(5), pp. 496–498, 1981.
Vanhove, D., Makambo, L., and Blanchard, M., Journal of Chemical Research (S), 10, p. 335, 1980.
Vanhove, D., Zhuyong, Z., Makambo, L., and Blanchard, M., Applied Catalysis, 9, pp. 327–342, 1984.
Niiyama, H., Nishiyama, S., Nakamura, R., and Echigoya, E., Pan-Pacific Synfuels Conference, V. 1, pp. 197–293, 1982.
Lisitsyn, A. S., Kuznetsoz, V. L., and Ermakov, Y. I., Kinetics and Catalysis, 23(4), pp. 777–782 and 783–787, 1983.
Twenty-Third Annual Spring Symposium of the Pittsburgh-Cleveland Catalysis Society.

*Primary Examiner*—Howard T. Mars
*Attorney, Agent, or Firm*—Roylance, Abrams, Berdo & Goodman

[57] ABSTRACT

Synthesis gas comprising carbon monoxide and hydrogen is converted to a liquid hydrocarbon by contacting the synthesis gas under conversion conditions with a catalyst prepared by subjecting a cobalt carbonyl-impregnated alumina or silica support to an activation procedure at a temperature not exceeding 500° C. comprising, in sequence, (A) reduction in hydrogen, (B) oxidation in an oxygen-containing gas, and (C) reduction in hydrogen.

17 Claims, No Drawings

ACTIVATED COBALT CATALYST AND SYNTHESIS GAS CONVERSION USING SAME

CROSS-REFERENCE TO RELATED APPLICATIONS

This application is a continuation-in-part of U.S. Ser. No. 635,911 filed July 30, 1984, which, in turn, is a continuation-in-part of U.S. Ser. No. 310,969 filed Oct. 13, 1981 abandoned and U.S. Ser. No. 540,662 filed Oct. 11, 1983, now U.S. Pat. No. 4,493,905 which, in turn, is a divisional of U.S. Ser. No. 310,977 filed Oct. 13, 1981, now U.S. Pat. No. 4,413,064, all in the name of H. Beuther et al.

FIELD OF THE INVENTION

The present invention relates to a process for the conversion of synthesis gas to liquid hydrocarbons in the presence of a supported cobalt carbonyl catalyst, to the preparation of such catalyst and to the catalyst, per se. More particularly, this invention relates to conversion of synthesis gas to liquid hydrocarbons using a cobalt carbonyl-impregnated refractory metal oxide support as catalyst that has been subjected to an activation treatment to provide improved activity and selectivity of the catalyst.

BACKGROUND INFORMATION

The growing importance of alternative energy sources has brought a renewed interest in the Fischer-Tropsch synthesis as one of the more attractive direct and environmentally acceptable paths to high quality transportation fuels. The Fischer-Tropsch synthesis involves the production of hydrocarbons by the catalyzed reaction of CO and hydrogen. Commercial plants have operated in Germany, South Africa and other parts of the world based on the use of particular catalysts.

The use of promoted cobalt catalysts has attracted wide attention. For example, the German commercial operation concentrated on the use of a precipitated cobalt-thoria-kieselguhr fixed-bed catalyst, and a later modification in which MgO, for economy reasons, replaced part of the thoria.

More recently, U.S. Pat. No. 4,088,671 to T. P. Kobylinski describes the use of a ruthenium-promoted cobalt catalyst on a support, such as alumina or kieselguhr, in the synthesis of hydrocarbons from the reaction of CO and hydrogen at substantially atmospheric pressure. As ruthenium is expensive, the patent indicates that it is preferred to employ ruthenium in the minimum amount necessary to achieve the desired result.

Attempts have been made to utilize unpromoted cobalt catalysts for the synthesis of hydrocarbons from synthesis gas. However, unpromoted cobalt often had poor selectivity and requires high metal loadings to provide desirable activity.

SUMMARY OF THE INVENTION

It has now been found in accordance with the present invention, that synthesis gas comprising hydrogen and carbon monoxide can be selectively converted under synthesis gas conversion conditions to liquid hydrocarbons with a catalyst prepared by subjecting a cobalt carbonyl-impregnated alumina or silica support to an activation procedure comprising the steps, in sequence, of (A) reduction in hydrogen, (B) oxidation in an oxygen-containing gas, and (C) reduction in hydrogen, the activation procedure being conducted at a temperature below 500° C. Surprisingly, it has been found that the activated, cobalt carbonyl-impregnated catalyst of the present invention provides very high reaction rates at moderate metal loadings, while at the same time, providing high selectivity, even without the use of the usual promoters. The catalyst of the present invention is produced by impregnating an alumina or silica support with a cobalt carbonyl and the impregnated support is subjected to an activation procedure including the steps of (i) reduction, (ii) oxidation, and (iii) reduction, herein termed "ROR activation" while under a temperature not exceeding 500° C. An unpromoted cobalt catalyst is produced having activity for synthesis gas conversion nearly comparable to conventional ruthenium-promoted catalysts made by impregnating cobalt nitrate on alumina, but without the ROR activation procedure of the present invention. Moreover, as will be hereinafter demonstrated, by subjecting the cobalt carbonyl impregnated catalyst to ROR activation, the resulting unpromoted catalyst produces as much $C_{5+}$ hydrocarbon product as do such ruthenium-promoted cobalt catalysts which have been subjected to ROR activation.

According to a preferred embodiment of the present invention, the supported dicobalt octacarbonyl catalyst of the present invention is prepared using a non-aqueous, organic solvent impregnation solution for depositing the cobalt octacarbonyl onto the support.

According to still another preferred embodiment of the present invention, promoter metals, such as ruthenium and lanthana and/or manganese oxide may be included with the catalyst.

DESCRIPTION OF THE PREFERRED EMBODIMENTS

The catalyst of the present invention is prepared by impregnating a support comprising a refractory oxide formed of alumina, in particular, gamma-alumina, eta-alumina or mixtures thereof, or silica with cobalt carbonyl. Any suitable cobalt carbonyl compound may be employed, including dicobalt octacarbonyl, $Co_2(CO)_8$, tetracobalt dodecylcarbonyl, $Co_4(CO)_{12}$, or the like.

The supported cobalt catalysts of the present invention are prepared by impregnation of a refractory oxide support using a non-aqueous impregnation solution of cobalt.

The catalyst can contain from about 1 to about 30 weight percent cobalt based upon total catalyst weight, preferably from about 3 to about 20 weight percent cobalt, with from about 5 to about 15 weight percent cobalt being especially preferred.

The refractory metal oxide support can be alumina or silica. Alumina is preferred, and the alumina is preferably a gamma or eta alumina. Likewise, extruded gamma or eta alumina can be used. The support of the present invention is characterized as having low acidity, a high surface area and high purity. The expression "low acidity" as used in the present application means that the support has a Brönsted activity with $H_o < 1.5$ which is less than 5 micromol per gram or about $10^{16}$ acid sites per square meter of surface area. The low acidity of the support is required in order to enable the catalyst to provide a higher molecular weight hydrocarbon product.

The surface area of the support of the present invention is at least 40 or 50 square meters per gram but is not so great as to become unduly microporous so as to permit reactant materials to enter the interstices of the catalyst. A suitable surface area is from about 40 to about 250, preferably from about 150 to about 225 square meters per gram. The deleterious effect of acidity is isomerization and cracking of intermediate olefins, removing them from chain growth and producing a low molecular weight product.

Although the unpromoted cobalt carbonyl on alumina or silica catalyst is extremely active for conversion of synthesis gas and highly selective for the production of $C_5+$ hydrocarbons, a promoter, such as ruthenium or the like may be included in the catalyst of the present invention if desired. The amount of ruthenium can be from about 0.01 to about 0.50 weight percent, preferably from about 0.05 to about 0.25 weight percent based upon total catalyst weight.

Surprisingly, it was found that the addition of a promoter, such as lanthanum or manganese reduces the activity of the unpromoted catalyst of the present invention, but increases such activity if used in addition to ruthenium. Thus, in accordance with a further embodiment of the present invention, the catalyst of the present invention may contain in addition to cobalt and ruthenium, from about 0.1 to 5 weight percent, preferably from about 0.1 to about 2 weight percent of a suitable promoter metal oxide, such as $La_2O_3$, $MnO_2$, or a Group IIIB or IVB metal oxide. Oxides of the lanthanides and actinides are preferred, and, thus, suitable metal oxides include, for example, $Sc_2O_3$, $Y_2O_3$, $Ac_2O_3$, $Pr_2O_3$, $PrO_2$, $Nd_2O_3$, $Sm_2O_3$, $Eu_2O_3$, $Gd_2O_3$, $Tb_2O_3$, $Tb_4O_7$, $Dy_2O_3$, $Ho_2O_3$, $Er_2O_3$, $Tm_2O_3$, $Yb_2O_3$, $Lu_2O_3$, $UO_2$, $UO_3$, $U_3O_8$, and the like. Especially preferred metal oxides for inclusion in the catalyst of the present invention include $La_2O_3$, $CeO_2$, $ZrO_2$, $TiO_2$, $HfO_2$, $ThO_2$, and unseparated rare earth oxide mixtures high in lanthanum, praseodymium, and neodymium. Additional preferred promoters are $MgO$ and $MnO_2$.

The preferred method employed to deposit the catalytic metals of the present invention onto the support involves the use of nonaqueous, organic impregnation solutions consisting essentially of the cobalt carbonyl and, if desired, a soluble promoter metal salt, e.g., ruthenium acetylacetonate, in order to achieve the necessary metal loading and distribution required to provide the highly selective and active catalyst of the present invention.

Initially, the support, such as alumina, is treated by oxidative calcination of the gamma and/or eta-alumina at a temperature in the range of from about 450° to about 900° C., preferably from about 600° to about 750° C. to remove water from the micropores of the support.

Meanwhile, non-aqueous organic solvent solution of cobalt carbonyl, and, if desired, non-aqueous organic solvent solutions of ruthenium, lanthanum, and/or manganese salts, for example, are prepared. Any suitable ruthenium salt, such as ruthenium nitrate, chloride, acetate or the like can be used. Ruthenium acetylacetonate is preferred. In addition, any suitable promoter metal, e.g., lanthanum salt, such as lanthanum nitrate or lanthanum acetate or manganese salt, such as manganese nitrate, or the like can be employed. In general, any metal salt which is soluble in the organic solvent of the present invention and will not introduce acidity or have a poisonous effect on the catalyst can be utilized. The non-aqueous organic solvent of the present invention is a non-acidic liquid which is formed from moieties selected from the group consisting of carbon, oxygen, hydrogen and nitrogen, and possesses a relative volatility of at least 0.1. The expression "relative volatility" as used in the present application is defined as the ratio of the vapor pressure of the solvent to the vapor pressure of acetone, as reference, when measured at 25° C.

Suitable solvents for dicobalt octacarbonyl are hydrocarbons, such as pentane, hexane and toluene; ethers, such as tetrahydrofuran; or mixtures of the foregoing solvents.

Suitable solvents for the promoter salts include, for example, ketones, such as acetone, butanone (methyl ethyl ketone); the lower alcohols, e.g., methanol, ethanol, propanol and the like; amides, such as dimethyl formamide; amines, such as butylamine; ethers, such as diethylether and tetrahydrofuran; hydrocarbons, such as pentane and hexane; and mixtures of the foregoing solvents. Tetrahydrofuran is the preferred solvent for cobalt carbonyl, and acetone is the preferred solvent for lanthanum or manganese nitrates and ruthenium acetylacetonate.

The amount of solvent utilized is an amount that is at least equivalent to the pore volume of the alumina utilized, but not greater than five times the alumina pore volume. For example, a commercially available gamma-alumina useful in the present invention has a pore volume of between about 0.2 to about 0.7 cubic centimeters pore volume per gram of alumina.

In accordance with the present invention, ruthenium and other promoter metal oxides are added in other impregnation steps, separately or in combination, before impregnations of the cobalt carbonyl.

Any suitable impregnation technique can be employed for the promoters including techniques well known to those skilled in the art so as to distend the catalytic metals in a uniform thin layer on the catalyst support. For example, they can be deposited on the support material by the "incipient wetness" technique. Such technique is well known and requires that the volume of impregnating solution be predetermined so as to provide the minimum volume which will just wet the entire surface of the support, with no excess liquid. Alternatively, the excess solution technique can be utilized if desired. If the excess solution technique is utilized, then the excess solvent present, e.g., acetone, is merely removed by evaporation. Thus, the impregnation solution can be added in excess, namely, up to five times the pore volume of the alumina, or can be added using just enough solution to fill the pore volume of the support.

Next, the impregnation solution and alumina are stirred while evaporating the solvent at a temperature of from about 25° to about 50° C. until "dryness".

The catalyst impregnated with promoters is slowly dried at a temperature of from about 110° to about 120° C. for a period of about one hour so as to spread the metals over the entire support. The drying step is conducted at a very slow rate in air.

The dried catalyst is calcined by heating slowly in flowing air, for example 10 cubic centimeters per gram of catalyst per minute, to a temperature in the range of from about 200° to about 400° C., preferably from about 250° to about 300° C., that is sufficient to decompose the metal salts and fix the metals. The aforesaid drying and calcination steps can be done separately or can be combined. However, calcination should be conducted by using a slow heating rate of, for example, 0.5° to about 3° C. per minute, preferably from about 0.5° to about 1° C. per minute and the catalyst should be held at the maximum temperature for a period of about one to about 20 hours, preferably for about 2 hours.

The foregoing impregnation steps are repeated with additional impregnation solutions in order to obtain the desired promoter metal loading. The calcined support is then impregnated in a dehydrated state with the non-aqueous, organic solvent solution of the cobalt carbonyl. Thus, the calcined support should not be unduly exposed to atmospheric humidity so as to become rehydrated. The impregnation technique used for dicobalt octacarbonyl may be the same as described above for the promoter salts, except that an oxygen-free water-free atmosphere, such as argon, helium or nitrogen, must be employed. Preferably, an incipient wetness technique is used so that the solvent may be removed easily. If more than one impregnation is required to achieve the desired metal loading, the cobalt carbonyl deposited in the first step must be decomposed by a reduction-reoxidation treatment, which are the first two steps of the "ROR"—activation treatment of the present invention. After the last impregnation sequence, the loaded catalyst support is then subjected to the reduction-oxidation-reduction activation treatment (ROR activation) of the present invention.

The ROR activation treatment of the present invention must be conducted at a temperature below 500° C. in order to achieve the dramatic increase in activity and selectivity of the cobalt carbonyl-impregnated catalyst. Temperatures of 500° C. or above reduce the liquid hydrocarbon selectivity of the present catalyst. Suitable activation temperatures are below 500° C., preferably below 450° C., and below 400° C. is especially preferred, e.g. 250° to 400° C. The impregnated catalyst is preferably slowly reduced in the presence of hydrogen. The reduction is best conducted in two steps wherein the first reduction heating step is carried out at a slow heating rate of no more than from about 0.5° to about 5° C. per minute, preferably from about 0.5° to about 1° C. per minute up to a maximum hold temperature of 200° to about 300° C., preferably 200° to about 250° C., for a hold time of from about 6 to about 24 hours, preferably from about 16 to about 24 hours under ambient pressure conditions. In the second reduction heating step, the catalyst can be heated at from about 0.5° to about 3° C. per minute, preferably from about 0.5° to about 1° C. per minute to a maximum hold temperature of from about 250° or 300° up to about 450° C., preferably from about 350° to about 400° C. for a hold time of 6 to about 65 hours, preferably from about 16 to about 24 hours. Although pure hydrogen can be employed for this reduction step, a mixture of hydrogen and nitrogen can be utilized in order to slowly reduce the catalyst. For example, the reduction step can be conducted initially using a gaseous mixture comprising 5% hydrogen and 95% nitrogen, and thereafter, the concentration of hydrogen can be gradually increased until pure hydrogen is obtained so as to slowly reduce the catalyst. Thus, slow reduction may involve the use of a mixture of hydrogen and nitrogen at 100° C. for about one hour; increasing the temperature 0.5° C. per minute until a temperature of 200° C.; holding that temperature for approximately 30 minutes; and then increasing the temperature 1° C. per minute until a temperature of 350° C. is reached and then continuing the reduction for approximately 16 hours. Reduction should be slow enough initially so that excessive volatilization of cobalt carbonyl does not occur and the flow of the reducing gas maintained high enough so that any water formed has a partial pressure in the offgas below one percent, so as to avoid excessive steaming of the exit end of the catalyst bed.

The reduced catalyst is passivated at ambient temperature (25°–35° C.) by flowing diluted air over the catalyst slowly enough so that a controlled exotherm passes through the catalyst bed. After passivation, the catalyst is heated slowly in diluted air to a temperature of from about 300° to about 350° C. in the same manner as previously described in connection with calcination of the catalyst.

Next, the oxidized catalyst is then slowly reduced in the presence of hydrogen in the same manner as previously described in connection with reduction of the impregnated catalyst. This completes the ROR activation treatment.

The composite catalyst of the present invention has an average particle diameter which depends upon the type of reactor to be utilized, of from about 0.01 to about 6 millimeters; preferably from about 1 to about 6 millimeters for a fixed bed; and preferably from about 0.01 to about 0.11 millimeters for a reactor with the catalyst suspended by gas, liquid, or gas-liquid media (e.g., fluidized beds, slurries, or ebullating beds).

The charge stock used in the process of this invention is a mixture of CO and hydrogen. Any suitable source of the CO and hydrogen can be used. The charge stock can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of this invention, but it may be present as a diluent gas. Sulfur compounds in any form are deleterious to the life of the catalyst and should be removed from the CO—$H_2$ mixture and from any diluent gases.

The reaction temperature is suitably from about 160° to about 350° C., preferably from about 175° to about 275° C., and most preferably from about 185° to about 250° C. The total pressure is, for example, from about 1 to about 100 atmospheres, preferably from about 3 to about 35 atmospheres, and most preferably from about 10 to about 20 atmospheres.

The gaseous hourly space velocity based upon the total amount of feed is less than 20,000 volumes of gas per volume of catalyst per hour, preferably from about 100 to about 5000 v/v/hour, with from about 1000 to about 2500 v/v/hour being especially preferred. If desired, pure synthesis gas can be employed or, alternatively, an inert diluent, such as nitrogen, $CO_2$, methane, steam or the like can be added. As used herein, the expression "inert diluent" indicates that the diluent is non-reactive under the reaction conditions herein disclosed or is a normal reaction product.

The synthesis gas reaction using the catalysts of this invention can occur in a fixed, fluid or moving bed type of operation.

The invention will be further described with reference to the following experimental work. All percentages will be in terms of weight percent unless otherwise indicated.

EXAMPLE 1

The preparation of the catalyst of the present invention is exemplified by the following description.

A catalyst (denoted "catalyst A") was prepared by impregnating 22.002 grams of a gamma-alumina (Ketjen EC commercially availably from Akzo Chemie) with 8.700 grams of dicobalt octacarbonyl in tetrahydrofuran in an oxygen-free atmosphere. The alumina was treated with acetone and calcined at 300° C. prior to impregnation. The catalyst was loaded into a reactor in a glovebox. Initially, the catalyst was activated by heating at 5° C. per minute in 1680 cubic centimeters per gram per hour of hydrogen to a temperature of 185° C. at which temperature the catalyst was held for one hour. The reduced weight of the catalyst was 12 weight percent cobalt and 88 weight percent alumina.

The catalyst was subjected to a two-day synthesis run in which the catalyst was contacted with hydrogen and carbon monoxide at a ratio of 1.85 at a temperature of 185° C. under a pressure of one bar at a synthesis gas flow rate of 1680 cubic centimeters per gram of catalyst per hour on the first day, and thereafter subjecting the catalyst to a synthesis run on the second day under the same conditions with the exception of a temperature of 195° C. and a hydrogen to carbon monoxide ratio of 1.5. Thereafter, the catalyst was purged in hydrogen at 185° C., and then heated at a rate of 1° C. per minute to a temperature of 350° C. and held at such temperature for a period of one hour (treatment to this point denoted "R350"). The catalyst was then subjected to another two days of synthesis at 185° C. and 195° C., respectively, under the conditions previously indicated, and then purged in hydrogen, and cooled in nitrogen to room temperature. While under room temperature conditions, the catalyst was dosed with 6 pulses of an air/nitrogen mixture. Next, oxidation of the catalyst was conducted in flowing air by heating at a temperature of 1° C. per minute until the catalyst reached 300° C. where it was held for a period of five and one-half hours. The catalyst was then purged in nitrogen and cooled. Finally, the catalyst was reduced once again by heating at a rate of 1° C. per minute in hydrogen until a temperature of 350° C. was reached and then holding at that temperature for five and one-half hours (treatment to this point denoted "ROR").

For comparative purposes, a catalyst containing 20 weight percent cobalt, 0.5 weight percent ruthenium and 1.0 weight percent $La_2O_3$ (catalyst B) prepared by impregnating gamma-alumina with cobalt nitrate rather than cobalt carbonyl, and a third catalyst containing 25 weight percent cobalt, 0.5 weight percent ruthenium and one weight percent lanthanum oxide (catalyst C) also impregnated using cobalt nitrate, rather than cobalt carbonyl, were tested at the same time and thus under the identical conditions of the aforesaid cobalt carbonyl catalyst (catalyst A).

The results of the foregoing tests made at 185° C. and a hydrogen to carbon monoxide ratio of 1.85 are set forth in Table I, below, while the results of tests made at 195° C. at a hydrogen to carbon monoxide ratio of 1.5 are set forth in Table II, below:

TABLE I

| Catalyst | CO Conversion Rate (cc/gram Co/hour) | | $C_5+$ Liquid (Wt. %) | |
|---|---|---|---|---|
| | R350 | ROR | R350 | ROR |
| A | 1230 | 1485 | 73 | 81 |
| B | 790 | 1190 | 80 | 79 |
| C | 690 | 960 | 81 | — |

The results set forth in Table I demonstrate that the ROR treatment of the cobalt carbonyl catalyst (catalyst A) produces a catalyst having an activity (1485 cubic centimeters per gram of cobalt per hour), which is much greater than that of promoted catalysts (790 cubic centimeters per gram of cobalt per hour for catalyst B and 690 cubic centimeters per gram of cobalt per hour for catalyst C). Additionally, the activated cobalt carbonyl catalyst A has a selectivity for the production of $C_5+$ hydrocarbon liquid comparable to the ruthenium-promoted cobalt catalyst.

TABLE II

| Catalyst | CO Conversion Rate (cc/gram Co/hour) | | $C_5+$ Liquid (Wt. %) | |
|---|---|---|---|---|
| | R350 | ROR | R350 | ROR |
| A | 1525 | 1730 | 67 | 73 |
| B | 1060 | 1415 | 80 | 72 |
| C | 860 | 1100 | 76 | 73 |

Upon viewing the results of Table II, it is seen that the ROR treatment greatly increased the activity of the cobalt carbonyl catalyst (catalyst A) while providing it with catalyst selectivity (73 weight percent $C_5+$), comparable to that of the promoted cobalt catalyst B (72 weight percent $C_5+$) and catalyst C (73 weight percent $C_5+$). Thus, Tables I and II clearly demonstrate that the combination of an ROR activation treatment of an unpromoted carbonyl catalyst provides a synthesis conversion catalyst having a greatly increased catalyst activity and a catalyst selectivity comparable to promoted cobalt catalysts having a much higher cobalt loading.

EXAMPLE 2

This example demonstrates the effect of incorporating a promoter into the cobalt carbonyl catalyst of the present invention.

Ruthenium-promoted cobalt carbonyl catalyst samples were prepared by impregnating an alumina support identical to that used in Example 1 with lanthanum nitrate in acetone. The impregnated support was dried to remove the solvent and then calcined for two hours at a temperature of 300° C. Next, ruthenium acetylacetonate in acetone was added and the catalyst reduced in hydrogen while being heated at a rate of 2° C. per minute until a temperature of 200° C. was reached. The catalyst was then maintained at 200° C. for two hours. This catalyst is denoted "catalyst D". Additional catalyst samples (denoted "catalyst E") were prepared in a manner identical to catalyst D except that the lanthanum nitrate addition step was omitted.

After reduction, the resulting catalyst sample was impregnated with dicobalt octacarbonyl in tetrahydrofuran, without exposure to air, and was stored in a controlled atmosphere glove-box. The catalyst was prepared to contain 12 weight percent cobalt and 0.3 weight percent ruthenium in the reduced state.

Next, hydrogen sorption measurements were performed in a static volumetric apparatus, and for each test, 2 gram samples were placed in chemisorption cells inside the glove-box and the cells were then sealed and transferred to the sorption unit. The catalysts were evacuated, then reduced in hydrogen as they were heated to 350° C. and held at that temperature for one hour. After evacuation at 350° C., the samples were cooled to room temperature for hydrogen sorption measurements. The sorption capacities at 100–500 torr were measured and the total sorption capacity was estimated by extrapolation to zero pressure.

Following the hydrogen sorption capacity measurements, the catalysts were evacuated, then passivated by dosing in air three times to 500 torr and they were then oxidized in flowing air while heating to 300° C. at a rate of 1° C. per minute and were held at that temperature for a period of five and one-half hours. Finally, they were again reduced overnight at 350° C. and their hydrogen sorption capacities were again measured.

The results of the hydrogen sorption and metal dispersion tests are set forth below in Table III:

TABLE III

| Catalyst | R350 | ROR |
|---|---|---|
| | Hydrogen Sorption Capacity (millimoles/gram) | |
| A | 0.242 | 0.112 |
| D | 0.234 | 0.169 |
| E | 0.231 | 0.190 |
| | Metal Dispersion H/(CO + Ru) | |
| A | 0.29 | 0.13 |
| D | 0.27 | 0.22 |
| E | 0.27 | 0.20 |

Measurements of hydrogen sorption capacities on the slurry catalysts made with dicobalt octacarbonyl showed that their metal dispersions were about 30 percent after mild reduction. That is about 1.5–2.0 times higher than dispersions obtained by impregnating cobalt nitrate on the same support. Dispersion dropped after ROR treatment, while synthesis activities increased. Activity increase after ROR treatment was not caused by improved metal dispersion, but by an increase in turnover frequency of the metal sites. In other words, the activity per metal site increased indicating that the ROR treatment has brought the catalyst to its most efficient activity per unit weight of metal.

Activity tests were made after similar reduction and ROR treatments, respectively. An 0.5 gram sample of each catalyst was treated in 5,000 cubic centimeters per gram per hour of flowing hydrogen in the reactor before each test. The activity tests were made at atmospheric pressure using 1680 cubic centimeters per gram per hour of synthesis gas flow and 185° C. at a hydrogen to carbon monoxide ratio of 1.85 for a period of 10 to 20 hours onstream. Activity tests were also made at a temperature of 195° C. at a hydrogen to carbon monoxide ratio of 1.5 under atmospheric pressure and a synthesis gas flow of 1680 cubic centimeters per gram per hour while onstream for 35–45 hours. After activity tests, the catalysts were purged in hydrogen for one hour at 185° C. to strip hydrocarbons, before they were given another activation treatment.

The results are set forth below in Tables IV and V:

TABLE IV

| | CO Conversion Rate (cc/gram Co/hour) | | $C_5+$ Liquid (Wt. %) | |
|---|---|---|---|---|
| Catalyst | R350 | ROR | R350 | ROR |
| A | 1230 | 1485 | 73 | 81 |
| D | 870 | 2050 | 79 | 80 |
| E | 1010 | 1905 | 67 | 79 |

TABLE V

| | CO Conversion Rate (cc/gram Co/hour) | | $C_5+$ Liquid (Wt. %) | |
|---|---|---|---|---|
| Catalyst | R350 | ROR | R350 | ROR |
| A | 1525 | 1730 | 67 | 73 |
| D | 1035 | 2170 | 70 | 72 |
| E | 1370 | 2030 | 62 | 71 |

As seen in Table IV, the $C_5+$ selectivity at 185° C. increased from 73 to 81 weight percent for the unpromoted cobalt on alumina catalyst (A) from 79 to 80 weight percent for the ruthenium-lanthanum-promoted cobalt catalyst (D) and from 67 to 79 weight percent for the ruthenium-promoted-cobalt catalyst (E). Thus, these data indicate that the incorporation of ruthenium, alone, or with lanthanum provides a significantly higher catalyst activity using the ROR activation treatment, whereas the selectivity of the unpromoted cobalt catalyst is comparable to that of the promoted cobalt catalyst.

Likewise, similar results are seen in Table V wherein comparable selectivities for $C_5+$ hydrocarbons were achieved for both promoted and unpromoted catalysts. However, catalyst activity was significantly improved using the ruthenium promoter, alone, or in combination with lanthanum.

EXAMPLE 3

This example demonstrates the effect of using a silica support rather than an alumina support in connection with the cobalt carbonyl catalyst of the present invention.

A catalyst was prepared in the same manner as "Catalyst D", as described in Example 2, with the exception that a fluid silica (commercially available as Ketjen F5) rather than a fluid alumina support was employed. Samples of this catalyst ("Catalyst F") were subjected to activity tests in the same manner as described in Example 2 for catalyst D at 185° C. in a hydrogen to carbon monoxide ratio of 1.85, which test results are set forth in Table VI, below, while the results of tests made at 195° C. at a hydrogen to carbon monoxide ratio of 1.5 are set forth in Table VII, below:

TABLE VI

| | CO Conversion Rate (cc/gram Co/hour) | | $C_5+$ Liquid (Wt. %) | |
|---|---|---|---|---|
| Catalyst | R350 | ROR | R350 | ROR |
| D | 870 | 2050 | 79 | 80 |
| F | 1074 | 2285 | 62 | 84 |

The results set forth in Table VI show that the use of a silica support provides a higher conversion rate than that achieved with alumina, but with lower $C_5+$ selectivity. However, the $C_5+$ selectivity is much improved by the ROR treatment.

TABLE VII

| | CO Conversion Rate (cc/gram Co/hour) | | $C_5+$ Liquid (Wt. %) | |
|---|---|---|---|---|
| Catalyst | R350 | ROR | R350 | ROR |
| D | 1035 | 2170 | 70 | 72 |
| F | 1455 | 2730 | 60 | 70 |

Upon viewing the results of Table VII, it is seen once again, that the carbonyl on silica catalyst is more active than the carbonyl on alumina, but at a sacrifice in selectivity. However, the use of an ROR treatment greatly increases the selectivity of the silica supported catalyst.

What is claimed is:

1. A process for the conversion of synthesis gas to a product containing liquid hydrocarbons with an, activated, supported catalyst prepared by the steps, in sequence, of
   (A) impregnating an alumina or silica support with a cobalt carbonyl, (B) subjecting said cobalt carbonyl-impregnated alumina or silica support to an activation procedure comprising the steps of, in sequence, (i) reduction in hydrogen, (ii) oxidation with an oxygen-containing gas, and (iii) reduction in hydrogen, said activation procedure being conducted at a temperature below about 450° C., to produce an, activated catalyst having an activity after said step (iii) that is greater than the activity of the catalyst after said step (i), and contacting a synthesis gas comprising hydrogen and carbon monoxide under synthesis conversion conditions with said, activated catalyst to form a product containing liquid hydrocarbons.

2. The process of claim 1 wherein said support is alumina.

3. The process of claim 1 wherein said cobalt carbonyl is $Co_2(CO)_8$.

4. The process of claim 1 wherein said oxidation step is conducted at a temperature in the range of between about 100° and about 400° C.

5. The process of claim 4 wherein said second reduction step (C) is conducted at a temperature in the range of from about 200° to about 450° C.

6. The process of claim 1 wherein said activation steps are conducted while heating at a rate of from about 0.5° to about 2° C. per minute.

7. The process of claim 1 wherein said catalyst contains from about 1 to about 30 weight percent cobalt.

8. The process of claim 1 wherein said cobalt carbonyl-impregnated support is formed by impregnating said support with a non-aqueous organic solution of cobalt carbonyl.

9. The process of claim 8 wherein said non-aqueous solvent is tetrahydrofuran.

10. The process of claim 1 wherein said activation is conducted at a temperature in the range of between about 100° and about 400° C.

11. The process of claim 1 wherein said catalyst additionally contains between about 0.05 and about 0.50 weight percent ruthenium.

12. The process of claim 1 wherein said catalyst consists essentially of cobalt on alumina.

13. The process of claim 1 wherein said process is conducted at a temperature of from about 185° to about 250° C. while under a pressure of from about 10 to about 20 atmospheres.

14. The process of claim 1 wherein said support is silica.

15. The process of claim 11 wherein said catalyst additionally contains a lanthanum or manganese promoter.

16. The process of claim 7 wherein said catalyst contains from about 3 to about 20 weight percent cobalt.

17. The process of claim 16 wherein said catalyst contains from about 5 to about 15 weight percent cobalt.

* * * * *